United States Patent [19]

Rossi et al.

[11] Patent Number: 4,766,251

[45] Date of Patent: Aug. 23, 1988

[54] PROCESS FOR THE PREPARATION OF ETHYNYLBENZALDEHYDES

[75] Inventors: Robert D. Rossi, Levittown, Pa.; Steven P. Fenelli, Hillsborough, N.J.

[73] Assignee: National Starch and Chemical Corporation, Bridgewater, N.J.

[21] Appl. No.: 84,261

[22] Filed: Aug. 11, 1987

Related U.S. Application Data

[63] Continuation-in-part of Ser. No. 894,142, Aug. 7, 1986, abandoned.

[51] Int. Cl.$^4$ .................. C07C 47/546; C07C 119/10
[52] U.S. Cl. ...................................... 568/436; 564/274
[58] Field of Search ........................ 568/436; 564/274

[56] References Cited

U.S. PATENT DOCUMENTS

| | | | |
|---|---|---|---|
| 4,178,430 | 12/1979 | Billow | 528/245 |
| 4,283,557 | 8/1981 | Walton | 564/272 |
| 4,336,362 | 6/1982 | Walton | 526/248 |

OTHER PUBLICATIONS

K.S.Y. Lau et al., J. Polymer Sci., Polymer Chem. Ed. 21, 3009, (1983).
W. B. Austin et al., J. Org. Chem. 46, 2280–2286, (1981).
E. Goldberg et al., JACS, vol. 77, 359–361, (1955).
J. Ojima et al., CA vol. 77, 126305m, (1972).
S. J. Havens et al., J. Org. Chem. 50, 1763–65, (1985).

Primary Examiner—Werren B. Lone
Attorney, Agent, or Firm—Edwin M. Szala; Ellen T. Dec

[57] ABSTRACT

A multi-step process for the preparation of ethynylbenzaldehydes from bromo- or iodobenzaldehydes is disclosed. The arylhalogen is replaced with a protected ethynyl compound which is subsequently cleaved by base to form the arylacetylene. The aldehydic functionality is preserved by formation of a corresponding Schiff's base or acetal, and its subsequent regeneration by treatment with aqueous acid.

8 Claims, No Drawings

PROCESS FOR THE PREPARATION OF ETHYNYLBENZALDEHYDES

This application is a continuation-in-part of Ser. No. 894,142 filed Aug. 7, 1986, abandoned.

BACKGROUND OF THE INVENTION

This invention relates to a process for the preparation of ethynylbenzaldehydes. In a further embodiment, the invention also relates to selected, novel intermediates formed in carrying out the process herein.

At least two processes for the preparation of the subject compounds have been disclosed in the prior art. In one such process described by K. S. Lau et al. in J. Polymer Sci., Polymer Chem. Ed. 21, 3009 (1983) and also by W. B. Austin et al. in J. Org. Chem. 46, 2280 (1981), a silane protected acetylene is reacted with 3-bromobenzaldehyde to form a protected intermediate which thereafter is cleaved to generate the desired 3-ethynylbenzaldehyde. Yields of 80% are reported. The main disadvantage of this two-step process lies in the use of a relatively expensive starting compound, ethynyltrimethyl silane, which makes the process too expensive for commercial use. Another process, described by J. Ojima et al. in Chem. Lett. (7), 633 (1972), also reported in CA Vol 77, 126305 m (1972), utilizes a time-consuming, multi-step process which suffers from low yields.

There is a need in the art for a process for preparing the subject compounds in high yields, utilizing relatively inexpensive starting compounds and reagents.

SUMMARY OF THE INVENTION

The present invention discloses a process for the preparation of ethynylbenzaldehydes of the structure:

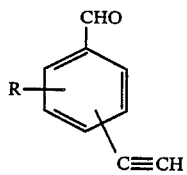

wherein R is H, $C_1$-$C_4$ alkyl, phenyl, nitro, Cl, F or —CHO.

In accordance with the invention, the process involves a synthesis or series of reaction steps to prepare intermediates relying on the use of a protected acetylene reagent and its coupling with the aromatic nucleus by means of the aryl halide. Removal of the protective group by alkali treatment generates the aryl acetylene. The process also relies on the preservation of the aldehydic group by means of primary amines (yielding Schiff's bases) or alcoholic functionalities (yielding acetals).

The process is useful for the preparation of ethynylbenzaldehydes which carry the ethynyl functionality in the 2, 3 or 4 position. The bromobenzaldehyde starting compound itself may be substituted with various substituent groups, for example, lower $C_1$-$C_4$ alkyl, phenyl, nitro, chlorine or fluorine, and —CHO, to yield the correspondingly substituted intermediates and end-product.

The ethynylbenzaldehydes described herein are useful as intermediates in the preparation of monomers which form electrically conducting polymers (see U.S. Pat. Nos. 4,283,557 and 4,336,362 to Walton, T. R.). Another use for these compounds is as capping groups in the preparation of high temperature stable polymers (see U.S. Pat. No. 4,178,430 to Bilow, N. and also the article by K. S. Lau referenced above).

In accordance with the process of the invention herein, the desired 2, or 3, or 4-ethynylbenzaldehyde (or substituted analog) is prepared by catalytically reacting a suitable bromobenzaldehyde starting compound with 2-methyl-3-butyn-2-ol or 3-methylpentyn-3-ol to provide a benzaldehyde carrying the protected acetylenic functionality. This intermediate is further reacted with phenylene diamine or other primary mono- or diamine to provide a second intermediate having a structure which effectively protects the aldehyde functionality. The second intermediate is treated with base to release an acetone molecule from the protected acetylene. The resultant intermediate, now carrying the free acetylenic group, is treated with aqueous acid to hydrolyze the imine bonds so as to yield the phenylene diamine salt and the desired ethynylbenzaldehyde.

The following schematically illustrates the sequence of reactions in the above-described process using 3-bromobenzaldehyde and phenylene diamine:

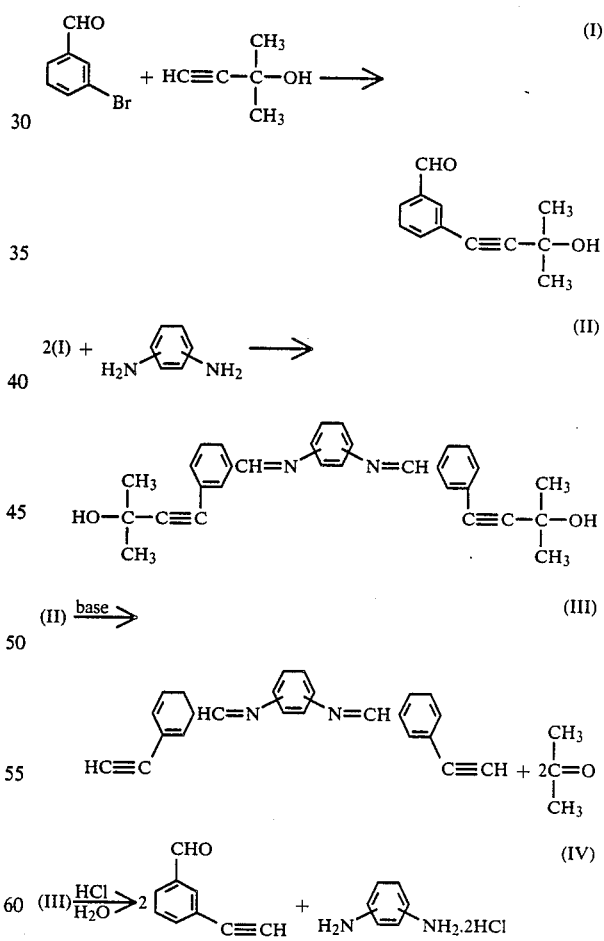

In a variation of the above reaction sequence it will be understood that the bromobenzaldehyde can first be reacted with the phenylene diamine to effectively preserve the aldehyde group. The protected acetylene reagent may then be coupled to this intermediate to yield (II) in the above reaction sequence. The desired ethynylbenzaldehyde is obtained by treatment of (II) with base to produce (III), and treatment of (III) with aqueous acid.

In another embodiment of the process herein, a bromobenzaldehyde starting compound is reacted with ethylene glycol in an organic solvent to provide an intermediate, 2-(3-bromophenyl)-1,3-dioxolane, in which the 1,3-dioxolane group effectively protects the aldehyde functionality. This intermediate is then reacted with 2-methyl-3-butyn-2-ol to provide a second intermediate carrying the capped acetylenic functionality. The second intermediate is treated with base to release acetone from the capped acetylene and generate the terminal aryl acetylene. In turn, the resultant intermediate is treated with aqueous acid to recover the aldehyde group from the protective 1,3-dioxolane substituent and yield the desired ethynylbenzaldehyde.

The following will schematically illustrate the sequence of reactions in the above-described process using 3-bromobenzaldehyde and ethylene glycol:

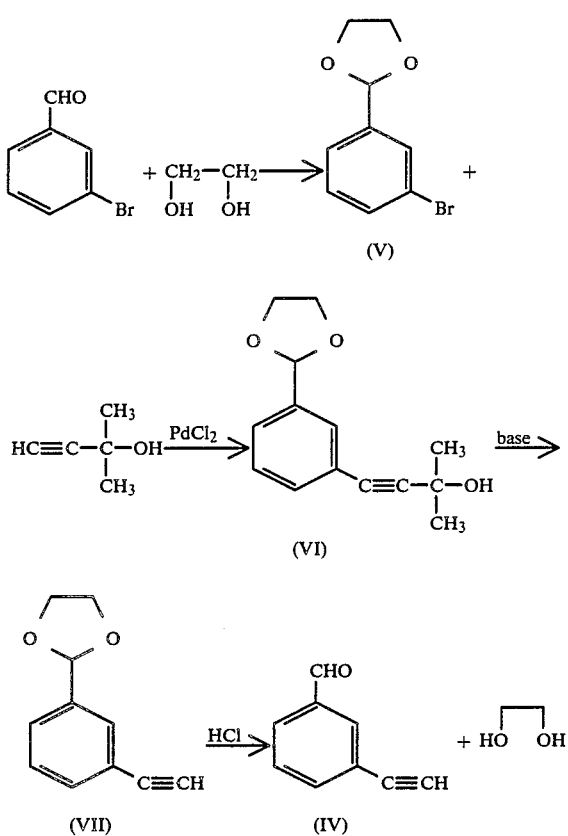

While the above reaction sequence shows the reaction of 3-bromobenzaldehyde and ethylene glycol to produce the cyclic acetal, a large number of variations are possible. Thus it is noted iodobenzaldehyde can be used in place of bromobenzaldehyde throughout the various reactions with comparable yields and efficiencies. Furthermore, the halogen may be in the 2-, 3-, or 4-position. Other cyclic acetals can also be prepared and used in this sequence. For example, propylene glycol and 1,3-propanediol as well as other diols may be used in place of ethylene glycol. Acyclic acetals are also useful and can be prepared using, for example, methanol, ethanol, n-propanol, isopropanol and n-butanol. Numerous examples of both cyclic and acyclic acetal preparation can be found in "Protective Groups In Organic Synthesis" by Theodora W. Greene, J. Wiley and Sons, Chap. 4 (1981).

Referring to the above reaction sequences, the intermediates designated (I) and (II) as well as (VI) and (VII) and their corresponding positional isomers and substituted analogs are novel compounds.

It is seen that the invention provides a process for the preparation of ethynylbenzaldehydes from bromo- or iodobenzaldehyde. The process relies on replacing the arylhalogen with a protected ethynyl compound which is subsequently cleaved to form the arylacetylene. Surprisingly, the preservation of the aldehydic group is easily affected by reaction to form the corresponding Schiff's base or alternatively by reaction with a mono- or dialcohol to form a corresponding acetal. The aldehydic group is regenerated by treatment of the protected substrate with aqueous acid.

DESCRIPTION OF PREFERRED EMBODIMENTS

The bromobenzaldehydes useful as starting materials herein may also be substituted with various substituent groups as earlier mentioned. Ordinarily, the substituent groups will play no part in the reaction sequences. While further descriptions will refer only to the unsubstituted species, it will be appreciated that reactions with the substituted species will not differ significantly.

With respect to the coupling reaction of the bromobenzaldehyde and the protected acetylene, 2-methyl-3-butyn-2-ol or 3-methylpentyn-3-ol, the reaction is run preferably with triethylamine which serves as a solvent and a scavenger for the hydrogen bromide generated during the ethynylation reaction. Other useful amines which can be used in place of triethylamine are, for example, diethylamine, butylamines (mono-, di, and trisubstituted), pyridine, and the like. A co-solvent such as toluene, xylene, dimethylformamide, and dimethylacetamide can also be used to improve the solubility of the starting materials. The reaction requires the presence of a catalytic amount of a palladium catalytic species which, for example, may be palladium acetate, palladium chloride, etc. Optionally, to hasten the coupling reaction a co-catalyst may also be used. Suitable co-catalysts include cuprous salts, for example, cuprous chloride, cuprous bromide, and cuprous iodide which is preferred. Use of palladium catalysts to promote coupling reactions of aromatic halides with acetylene compounds is described in the literature, for example, Richard F. Heck, *Palladium Reagents in Organic Syntheses,* Academic Press, New York 1985, Chapter 6, Section 6.8.1. Additionally, to improve the utility of the palladium catalyst, a solubilizing phosphine ligand is often used. Examples of such phosphine ligands include triorthotolulylphosphine and triphenylphosphine which is preferred because of its availability and cost.

The reaction is run in an inert atmosphere at atmospheric pressure at a temperature of 75°–85° C. for about 6–18 hours. The reaction is monitored by gas-liquid chromatography tracking the disappearance of starting material and/or appearance of product.

Aromatic primary diamines are preferred for use in protecting the aldehydic functional group, due particularly to their low cost, ready availability, ease of handling, economy in the process and high yields. In addition to the preferred phenylene diamine, also preferred are methylene dianiline and oxydianiline, so-called "bridged" phenylene diamines. Also useful are other "bridged" phenylene diamines, for example, where the bridging group is selected from sulfur, sulfone, isopropylidene, hexafluoroisopropylidene, dimethylsilane, dioxyphenylene, etc. The phenylene moiety may be substituted for example, with $C_1$–$C_4$ alkyl, bromine or chlorine. Other amines such as aromatic primary monoamines and, less preferably, some aliphatic primary mono- and diamines may also be used. Examples of aliphatic diamines include ethylene diamine and 1,4-cyclohexane diamine. It is only necessary that the imine group or Schiff's base produced by a selected amine be able to withstand the strongly alkaline conditions which are subsequently required to liberate the protected acetylene.

Ordinarily the reaction with an appropriate amine is carried out in an alcoholic medium. Conveniently this may be ethanol, methanol, isopropanol, or mixtures, in accordance with known procedures for producing a Schiff's base. It is noted that an acid catalyst such as is sometimes used in this reaction is not required. The resultant Schiff's base will conveniently precipitate from the alcoholic medium as it forms. The product is separated by filtration or centrifugation.

Cleavage of the protected acetylene on the Schiff's base is carried out by introducing the compound into an aromatic solvent, typically toluene or xylene, and the addition of solid alkali. Ordinarily 2–10%, preferably 3–6%, of solid alkali, such as sodium or potassium hydroxide by weight of the Schiff's base is sufficient. The cleavage reaction proceeds rapidly and is usually completed by refluxing for 30–60 minutes. The reaction is monitored by gas-liquid chromatography. When the cleavage is completed, the solution is cooled, the base is removed by filtration and the solvent is stripped off, and the crude residue is exposed to aqueous acid to liberate the aldehydic functionality. Any common mineral acid may be used and hydrochloric acid is preferred. The desired product precipitates from the aqueous acid, and the diamine (or amine) is solubilized as the acid salt. The product is separated by filtration or centrifugation and ordinarily will have a purity greater than 95%. Advantageously, the diamine (or amine) may be easily recovered and recycled into the process.

With respect to the process variation where the aldehydic functionality is protected by the acetal group, formation of acetals is well known and documented, and the acetals are formed herein using such known procedures. Subsequent reactions of the compounds containing these acetal radicals to provide the acetylenic functionality and thereafter recover the aldehydic functionality are carried out substantially as already described with respect to the process using the diamine (or amine) intermediate.

Summarizing, with respect to new compounds, it is seen that the present process provides new compounds of the following structures (a) and (b):

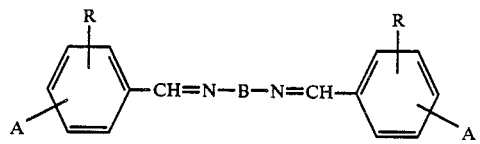

(a)

wherein
A is

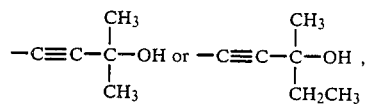

and
R is H, $C_1$–$C_4$ alkyl, phenyl, nitro, Cl, or F; and
B is ethylene, 1,4-cyclohexane, phenylene and

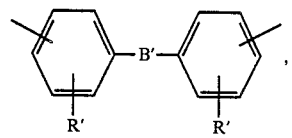

wherein B' is —CH$_2$—, —O—, —S—, —S(O)$_2$—, —C(CF$_3$)$_2$—, —C(CH$_3$)$_2$—, —Si(CH$_3$)$_2$— or

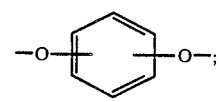

and
R' is H, $C_1$–$C_4$ alkyl, Cl or Br; and

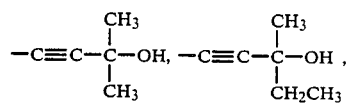

(b)

wherein
A is

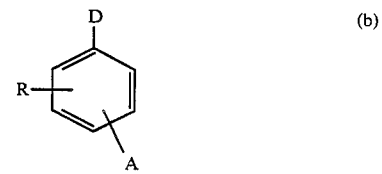

or —C≡CH,
D is a cyclic acetal radical, and
R is H, $C_1$–$C_4$ alkyl, phenyl, nitro, Cl, or F.

The compounds identified above have a primary use as intermediates in the preparation of ethynylbenzaldehydes by the process of the present invention.

This invention is further illustrated in connection with the following examples.

EXAMPLE I

Preparation of 4-(3-Hydroxy-3-methylbutynyl)benzaldehyde

A multinecked, round bottom flask fitted with a mechanical stirrer, reflux condenser, and thermometer, was flushed and maintained under a positive pressure of argon. The flask was charged with 50 g (0.27 mol) of 4-bromobenzaldehyde, about 225 ml of dried, degassed triethylamine, and 25.2 g (0.3 mol) of degassed 2-methyl-3-butyn-2-ol. To this solution was added 0.21 g (0.30 mol) of bis-triphenylphosphine palladium (II) chloride and 0.99 g (3.81 mmol) of triphenylphosphine. The stirred solution was heated to 60° C. at which point 0.05 g (0.26 mmol) of copper (I) iodide was introduced. The solution was further warmed to 80° C. and maintained at this temperature for 18–20 hours. At this point gas chromatography indicated about 98% conversion to product.

The mixture was diluted with about 200 ml of anhydrous ether and filtered to remove the precipitated triethylamine hydrobromide (48 g, 0.26 mol, 97.7% yield). The filtrate was concentrated on a rotary evaporator to a dark colored oil. The crude product was used in the preparation of the corresponding Schiff's base without further purification.

Analysis: IR (neat), 3400 cm$^{-1}$ (—OH, broad), 2230 cm$^{-1}$ (C≡C, weak), 1690 cm$^{-1}$ (—CHO).

EXAMPLE II

Preparation of Schiff's Base of 4-(3-Hydroxy-3-methyl butynyl)benzaldehyde and m-Phenylene diamine A multinecked, round bottom flask with a mechanical stirrer, reflux condenser, and a thermometer was flushed and maintained under a positive pressure of argon. The flask was charged with 50 g (0.265 mol) of the aldehyde from Example I and about 200 ml of isopropyl alcohol. To this solution was added, in small portions, 12.8 g (0.119 mol) of m-phenylene diamine. Upon complete addition of the diamine, the solution was heated to 50° C. for 5 minutes and then allowed to cool to room temperature. At about 30° C. the product began to precipitate as a yellow solid. The resulting slurry was allowed to stir overnight at room temperature.

The yellow solid was isolated by suction filtration and washed on the funnel with cold isopropanol. The product was dried in a vacuum oven overnight at about 40° C. to yield 43 g (0.096 mol, 80.7% yield) of dry product. This compound was used without further purification in the cleavage reaction (to provide the acetylene radical) shown in the next example.

Analysis: IR (KBr pellet), 3400 cm$^{-1}$ (OH, broad), 1625 cm$^{-1}$ (C̲H̲=N̲).

EXAMPLE III

Preparation of Schiff's Base of 4-Ethynylbenzaldehyde and m-Phenylene diamine

A multinecked, round bottom flask fitted with a mechanical stirrer, thermometer, and a Vigreux column attached to a distillation head was flushed and maintained under a positive pressure of argon. The flask was charged with 40 g (0.089 mol) of the product from Example II, about 200 ml of toluene, and 1.2 g (3% by weight) of potassium hydroxide. The mixture was heated slowly until the vapor temperature reached 110° C. Starting with a vapor temperature of about 60° C., a mixture of acetone and toluene was continuously removed by distillation. When the vapor temperature equilibrated at 110° C., the mixture was cooled to 60° C. and filtered to remove the potassium hydroxide. The filtrate was concentrated on a rotary evaporator to yield the product (Schiff's base of 4-ethynylbenzaldehyde and m-phenylene diamine) as a yellow solid. The product was washed with low-boiling petroleum ether, filtered and funnel dried to yield 28.3 g of purified product (0.085 mol, 95.5% yield).

Analysis: IR (KBr pellet), 3310 cm$^{-1}$ and 3290 cm$^{-1}$ (C≡C̲H̲), 1620 cm$^{-1}$ (C̲H̲=N̲).

$^1$HMR (CDCl$_3$) δ 8.45 (s, 2H, C̲H̲=N), 6.9–8.6 (m, 12H, Ar—H̲), 3.15 (s, 2H, C≡C̲H̲) ppm.

DSC (10° C./min, N$_2$) onset 141.6° C., minimum 150.6° C. (endothermic transition 123 J/g), onset 178.9° C., maximum 197.7° C. (exothermic transition 527 J/g).

EXAMPLE IV

Preparation of 4-Ethynylbenzaldehyde

A multinecked, round bottom flask fitted with a magnetic stirrer, reflux condenser, and thermometer, was charged with 5 g (0.015 mol) of the product of Example III and about 100 ml of distilled water. To this stirred mixture was added 1.1 g (30.6 mmol) of concentrated hydrochloric acid. The mixture was brought to 50° C. for about 4 hours and then cooled to room temperature which yielded the product as a yellow precipitate. The product was filtered, washed with distilled water and allowed to dry on the funnel overnight to yield 3 g (0.026 mol, 87% yield) of the purified product.

Analysis: IR (KBr pellet), 3290 cm$^{-1}$ and 3230 cm$^{-1}$ (C≡C̲H̲), 1690 cm$^{-1}$ (—CHO).

$^1$HMR(CDCl$_3$) δ 10.0 (s, 1H, CHO), 7.3–8.1 (m, 4H, Ar—H), 3.3 (s, 1H, C≡C̲H̲) ppm.

DSC (10° C./min, N$_2$) onset 85.7° C., minimum 90.8° C. (endothermic transition 161 J/g), onset 174.1° C., maximum 214.5° C. (exothermic transition 1105 J/g).

EXAMPLE V

Preparation of 3-(3-Hydroxy-3-methylbutynyl)benzaldehyde

A multinecked, round bottom flask fitted with a mechanical stirrer, reflux condenser and thermometer, was flushed and maintained under a positive pressure of nitrogen. The flask was charged with 164 g (0.89 mol) of freshly distilled 3-bromobenzaldehyde, about 450 ml of dried, degassed triethylamine and 81.5 g (0.97 mol) of degassed 2-methyl-3-butyn-2-ol. To this solution was added 0.7 g (1.0 mmol) of bis-triphenylphosphine palladium (II) chloride and 3.2 g (12.2 mmol) of triphenylphosphine. The stirred solution was heated to 60° C. at which point 0.1 g (0.52 mmol) of copper (I) iodide was introduced. The solution was further warmed to 80° C. and maintained at this temperature for 16–18 hours. At this point gas chromatography indicated 95–97% conversion to product.

The solution was diluted with about 200 ml of anhydrous ether and filtered to remove the precipitated triethylamine hydrobromide (159 g, 0.8 mol, 99% yield). The filtrate was concentrated on a rotary evaporator to a dark colored oil. The crude oil was vacuum distilled to yield 118.5 g (0.63 mol, 71% yield) of yellow product having a b.p. of 150°–165° C. at 4.5 mm of Hg, and solidified on standing.

Analysis: IR (KBr pellet), 3400 cm$^{-1}$ (—OH), 1685 cm$^{-1}$ (—CHO).

$^1$HMR (CDCl$_3$), δ 9.98 (s, 1H, CH̲O), 7.70 (m, 4H, aromatic H's ), 2.23 (broad s, 1H, OH̲), and 1.64 (s, 6H, C(C̲H̲$_3$)$_2$) ppm.

$^{13}$CMR (CDCl$_3$), δ 191.4, 136.9, 136.2, 128.7, 128.7, 123.9, 95.7, 80.3, 65.2, 31.2 ppm.

DSC (10° C./min, N$_2$) onset 55.2° C., minimum 58.9° C. (endothermic transition, 134 J/g).

EXAMPLE VI

Preparation of Schiff's Base of 3-(3-Hydroxy-3-methylbutynyl)benzaldehyde and p-Phenylene diamine A multinecked, round bottom flask fitted with a mechanical stirrer, reflux condenser and thermometer, was flushed and maintained under a positive pressure of nitrogen. The flask was charged with about 300 ml of a 50:50 mixture of isopropyl alcohol and isobutyl alcohol, and 83 g (0.44 mol) of the aldehyde from the previous example. To this solution was added, in small portions, 22.7 g (0.21 mol) of p-phenylene diamine. Upon complete addition of the diamine, the solution was heated to 50° C. for 5 minutes and then allowed to cool to room temperature. At about 30° C. the product began to precipitate as a yellow solid. The resulting slurry was allowed to stir overnight at room temperature.

The yellow solid was isolated by suction filtration and washed on the funnel with the isopropyl-isobutyl alcohol mixture described above. The product was dried in a vacuum oven overnight at 40° C. to yield 85 g (0.19 mol, 90.4% yield) of dry product. The product can be further purified by recrystallization from hot n-heptane.

Analysis: IR (KBr pellet), 3360 cm$^{-1}$ (broad, OH), 1620 cm$^{-1}$ (CH=N).

$^1$HMR (CDCl$_3$) δ 8.47 (s, 2H, CH=N), 7.70 (m, 12H, aromatic H's), 2.07 (s, 1H, OH) and 1.64 (s, 12H, C(CH$_3$)$_2$) ppm.

$^{13}$CMR (CDCl$_3$) δ 158.6, 149.9, 136.5, 134.2, 131.9, 128.7, 128.5, 123.7, 121.9, 94.7, 81.6, 65.6, 31.5 ppm.

DSC (10° C./min, N$_2$) onset 137.5° C., minimum 141.0° C. (endothermic transition 90.6 J/g), onset 303.9° C., maximum 341.4° C. (exothermic transition 642 J/g). Elemental analysis, calculated: %C 80.33, %H 6.29, %N 6.24, found: %C 80.51, %H 6.41, %N 5.96.

EXAMPLE VII

Preparation of Schiff's Base of 3-Ethynylbenzaldehyde and p-Phenylene diamine

A multinecked, round bottom flask fitted with a mechanical stirrer, thermometer and Vigreux column attached to a distillation head was flushed and maintained under a positive pressure of nitrogen. The flask was charged with 250 ml of toluene, 55.5 g (0.124 mol) of the product of Example VI and 1.5 g (3% by weight) of potassium hydroxide. The mixture was heated slowly until the vapor temperature reached 110° C. Starting with a vapor temperature of about 60° C., a toluene/acetone mixture was removed by distillation. When the vapor temperature equilibrated at 110° C., the mixture was cooled to about 85° C., and filtered hot to remove the potassium hydroxide. The filtrate was concentrated on a rotary evaporator to yield the product, Schiff's base of 3-ethynylbenzaldehyde and p-phenylene diamine, as a yellow solid. The product was washed with petroleum ether (30°-60° C.), suction filtered and dried on a sintered glass funnel. The product was recrystallized from hot toluene to yield 40.5 g of purified product (0.122 mol, 98.4% yield).

Analysis: IR (KBr pellet), 3270 cm$^{-1}$ (C≡CH), 1620 cm$^{-1}$ (CH=N). $^1$HMR (CDCl$_3$) δ 8.3 (s, 2H, CH=N), 7.70 (m, 12H, aromatic H's) and 3.1 (s, 2H, C≡CH) ppm.

$^{13}$CMR (CDCl$_3$) δ 158.5, 149.8, 136.4, 134.7, 132.5, 128.8, 122.5, 121.9, 82.9, 77.9 ppm.

DSC (10° C./min, N$_2$) onset 163.0° C., minimum 165.8° C. (endothermic transition 151 J/g), onset 207.5° C., maximum 223.1° C. (exothermic transition 676 J/g).

EXAMPLE VIII

Preparation of 3-Ethynylbenzaldehyde

A multinecked, round bottom flask fitted with a magnetic stirrer, reflux condenser, and a thermometer, was flushed and maintained under a positive pressure of nitrogen. The flask was charged with 1 g (3.00 mmol) of the product of Example VII and 50 ml of distilled water. To this stirred mixture was added 0.60 g (6.12 m mol) of concentrated hydrochloric acid. The mixture was brought to about 60° C. at which point about 25 ml of isopropyl alcohol was added to effect complete solution of the solid. The solution was cooled to room temperature and diluted with 200 ml of distilled water to ensure complete precipitation of the product as a yellow solid. The product was isolated by filtration and dried by washing with petroleum ether (30°-60° C.). The yield of dry product was 0.75 g (5.8 mmol, 95% yield).

Analysis: IR (KBr pellet), 3250 cm$^{-1}$ (C≡CH), 1700 cm$^{-1}$ (CHO).

$^1$HMR (CDCl$_3$) δ 10.0 (s, 1H, CHO), 7.70 (m, 4H, aromatic H's), and 3.20 (s, 1H, C≡CH) ppm.

$^{13}$CMR (CDCl$_3$) δ 191.1, 137.5, 136.4, 133.3, 129.3, 129.0, 123.3, 82.1, 78.8 ppm.

DSC (10° C./min. N$_2$) onset 73.1° C., minimum 75.8° C. (endothermic transition 178 J/g), onset 204.2° C., maximum 242.3° C. (exothermic transition 1110 J/g).

EXAMPLE IX

Preparation of 2-(3-Bromophenyl)-1,3-dioxolane

A multinecked, round bottom flask fitted with a mechanical stirrer, thermometer, and a Dean-Stark trap attached to a reflux condenser, was flushed and maintained under a positive pressure of nitrogen. The flask was charged with 300 g (1.62 mol) of 3-bromobenzaldehyde, 110.4 g (1.78 mol) of ethylene glycol, 550 ml of toluene, and 0.1 g (0.03 wt. % based on aldehyde) of p-toluene sulfonic acid monohydrate.

The system was brought to reflux temperature to initiate azeotropic distillation. The mixture was refluxed for about 11 hours at which point, gas chromatography indicated no starting aldehyde was present in the reaction mixture and the theoretical amount of water had been obtained.

The system was cooled to room temperature and 300 ml of 10% aqueous sodium hydroxide solution was added to the flask. The resulting bi-phase mixture was allowed to stir for one-half hour and was then poured into a separatory funnel. The aqueous layer was separated and discarded, and the organic product layer was washed with another 300 ml portion of 10% aqueous sodium hydroxide solution followed by several washings with water. The organic layer was dried over anhydrous potassium carbonate overnight and then filtered to remove the solid alkali.

The filtrate was concentrated on a rotary evaporator and distilled under reduced pressure. The fraction boiling at 107°-110° C./3 mm Hg was collected thus yielding 328 g (1.4 mol, 88% yield) of the product as a clear, water-white liquid of >99% purity as measured by gas chromatography.

Analysis: $^1$HMR (CDCl$_3$) δ 7.45 (m, 4H, Ar—H̲), 5.75 (s, 1H, benzylic), 4.05 (s, 4H, —O—CH̲$_2$—CH̲$_2$—O—) ppm.

EXAMPLE X

Preparation of 2-[3-(3-Hydroxy-3-methylbutynyl)phenyl]-1,3-dioxolane

A multinecked, round bottom flask fitted with a mechanical stirrer, thermometer, and a reflux condenser was flushed and maintained under a positive pressure of nitrogen. The flask was charged with 106 g (0.46 mol) of 2-(3-bromophenyl)-1,3-dioxolane prepared in the previous example, 350 ml of dried, degassed triethylamine, and 46.2 g (0.55 mol) of 2-methyl-3-butyn-2-ol. To this solution was added 0.36 g (0.51 mmol) of bis-triphenylphosphine palladium (II) chloride and 1.7 g (6.48 mmol) of triphenylphosphine. The stirred solution was heated to 60° C. at which point 0.1 g (0.52 mmol) of copper (I) iodide was introduced. The stirred solution was further warmed to 80° C. and maintained at this temperature for 18-20 hours. Gas chromatography indicated about 98% conversion to product.

The mixture was diluted with about 250 ml of anhydrous ether and then filtered to remove the precipitated triethylamine hydrobromide (83 g, 0.45 mol, 97.8% yield). The filtrate was concentrated in a rotary evaporator to a viscous oil. The crude product was used in the preparation of the corresponding Schiff's base without further purification.

Analysis: IR (neat), 3420 cm$^{-1}$ (—OH, broad), 1100 cm$^{-1}$ (—C—O—C—, strong). $^1$HMR (CDCl$_3$) δ 6.8–8.0 (m, 4H, Ar—H̲), 5.8 (s, 1H, benzylic), 4.1 (s, 4H, —O—CH̲$_2$—CH̲$_2$—O—), 1.65 (s, 6H, C(CH̲$_3$)$_2$) ppm.

EXAMPLE XI

Preparation of 2-(3-Ethynylphenyl)-1,3-dioxolane

A multinecked, round bottom flask fitted with a mechanical stirrer, thermometer and a Vigreux column attached to a distillation head was flushed and maintained under a positive pressure of nitrogen. The flask was charged with 90 g (0.39 mol) of the compound prepared in the previous example, about 300 ml of toluene, and 2.7 g (3% by weight) of potassium hydroxide. The mixture was heated slowly until the vapor temperature reached 110° C. Starting with a vapor temperature of about 60° C., a toluene/acetone mixture was removed by distillation. When the vapor temperature equilibrated at 110° C., the mixture was cooled to room temperature and filtered to remove the potassium hydroxide. The filtrate was concentrated on a rotary evaporator to a dark colored oil. The oil was vacuum distilled collecting the fraction boiling at 98°-100° C. at 2 mm Hg. The clear, yellow liquid product, 50.4 g (0.29 mol, 74.3% yield) was >99% pure as measured by gas chromatography. The product crystallized on standing.

Analysis: IR (KBr pellet) 3300 cm$^{-1}$ (C≡CH̲), 1100 cm$^{-1}$ (—C—O—C— strong).

$^1$HMR (CDCl$_3$) δ 7.5 (m, 4H, Ar—H̲), 5.75 (s, 1H, benzylic), 4.05 (s, 4H, —O—CH̲$_2$—CH̲$_2$—O—), 3.2 (s, 1H, C≡CH̲) ppm.

DSC (10° C./min. N$_2$) onset 51.8° C., minimum 54.2° C. (endothermic transition, 127 J/g); onset 205.0° C., maximum 239.8° C. (exothermic transition, 899 J/g).

EXAMPLE XII

Preparation of 3-Ethynylbenzaldehyde

A multinecked, round bottom flask fitted with a mechanical stirrer, reflux condenser and thermometer, was charged 50.4 g (0.289 mol) of the product of Example XI, 400 ml of distilled water and 1 of concentrated hydrochloric acid. The mixture was heated to 60° C. and maintained at that temperature for about 4 hours and then cooled to room temperature which yielded the product as a yellow precipitate. The product was filtered, washed with distilled water and allowed to dry on the funnel overnight to yield 33 g (0.254 mol, 87.8% yield).

Analysis of product was substantially identical to that obtained for the product of Example VIII.

EXAMPLE XIII

Preparation of Schiff's base of 3-(3-Hydroxy-3-methylbutynyl)benzaldehyde and 4,4'-methylene dianiline A multinecked, round bottom flask fitted with a reflux condenser, thermometer, magnetic stirrer, and a positive pressure of nitrogen, was charged with 5.3 g (0.028 mol) of 3-(3-hydroxy-3-methylbutynol)benzaldehyde, 30 ml of isopropyl alcohol, and 2.5 g (0.013 mol) of 4,4'-methylene dianiline. The mixture was heated and held at 60° C. for a half-hour, cooled to room temperature, and allowed to stir overnight. The resulting yellow precipitate was collected by suction filtration, and dried on the funnel to yield 4.3 g of product (0.012 mol, 92% yield).

Analysis: IR (KBr pellet), 3370 cm$^{-1}$ (OH, broad), 1630 cm$^{-1}$ (CH̲=N).

$^1$HMR (CDCl$_3$) δ 8.35 (s, 2H, CH̲=N), 7.0–8.0 (m, 16H, Ar—H̲), 3.9 (s, 2H, CH$_2$), 2.2 (broad s, 2H, —OH), 1.55 (s, 12H, C(CH̲$_3$)$_2$ ppm.

DSC (10° C./min, N$_2$) onset 122.0° C., minimum 129.9° C. (endothermic transition 62.4 J/g).

EXAMPLE XIV

Preparation of Schiff's base of 3-(3-Hydroxy-3-methylbutynyl)benzaldehyde and 4-aminophenyl ether Following the procedure of Example XIII, 2.6 g (0.013 mol) of 4-aminophenyl ether was used in place 4,4'-methylene dianiline. A yellow precipitate was collected by suction filtration and dried on the funnel to yield 4.4 g of product (0.012 mol, 92% yield).

Analysis: IR (KBr pellet) 3400 cm$^{-1}$ (OH, broad), 1630 cm$^{-1}$ (CH̲=N). $^1$HMR (CDCl$_3$) δ 8.35 (s, 2H, CH̲=N), 6.8–8.0 (m, 16H, Ar—H̲), 2.2 (broad s, 2H, OH̲), 1.55 (s, 12H, C(CH̲$_3$)$_2$ ppm.

Now that the preferred embodiments have been described in detail, various modifications and improvements thereon will become readily apparent to those skilled in the art. Accordingly, the spirit and scope of the present nvention are to be limited only by the appended claims, and not by the foregoing specification.

What is claimed is:

1. A multi-step process for preparing ethynylbenzaldehyde having the structure:

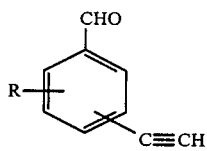

wherein R is H, C₁-C₄ alkyl, phenyl, nitro, Cl, F or —CHO, which comprises the steps of:
(a) reacting bromobenzaldehyde or substituted bromobenzaldehyde with 2-methyl-3-butyn-2-ol or 3-methylpentyn-3-ol in the presence of a palladium catalyst to replace the bromine with the protected ethynyl functionality,
(b) reacting the product of (a) with a primary mono- or diamine to form the corresponding Shiff's base,
(c) treating the product of (b) with solid alkali to cleave the acetone from the protected ethynyl functionality and thereby form the arylacetylene,
(d) treating the product of (c) with aqueous acid to recover the aldehyde group and thereby form the desired ethynylbenzaldehyde.

2. The process of claim 1 wherein the primary mono- or diamine of step (b) is selected from the group phenylene diamine, methylene dianiline and oxydianiline.

3. The process of claim 1 wherein step (a), the bromobenzaldehyde or substituted bromobenzaldehyde is reacted with 2-methyl-3-butyn-2-ol or 3-methylpentyn-3-ol employing triethylamine as solvent.

4. The process of claim 1 wherein step (a) the bromobenzaldehyde or substituted bromobenzaldehyde is first reacted with a primary mono- or diamine to form the corresponding Schiff's base and said Schiff's base is reacted with 2-methyl-3-butyn-2-ol or 3-methylpentyn-3-ol in the presence of a palladium catalyst to replace the bromine with the protected ethynyl functionality.

5. A compound of the structure (a) or (b):

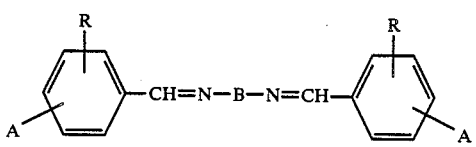

wherein
A is

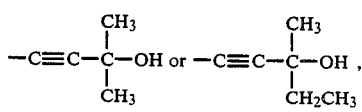

and
R is H, C₁-C₄ alkyl, phenyl, nitro, Cl or F; and
B is ethylene, 1,4-cyclohexane, phenylene and

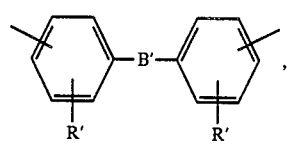

wherein B' is —CH₂—, —O—, —S—, —S(O)₂—, —C(CF₃)₂—, —C(CH₃)₂—, —Si(CH₃)₂— or

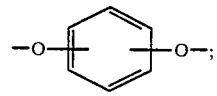

and R' is H, C₁-C₄ alkyl, Cl or Br; and

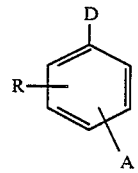

wherein
A is

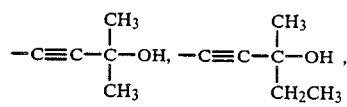

or —C≡CH,
R is H, C₁-C₄ alkyl, phenyl, nitro, Cl or F, and
D is a cyclic acetal radical.

6. A compound of claim 5 wherein structure (a), A is

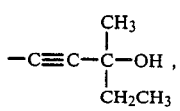

R is H and B is phenylene or

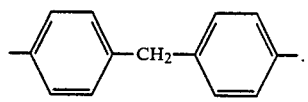

7. A compound of claim 5 wherein structure (a), A is

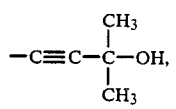

R is H and B is

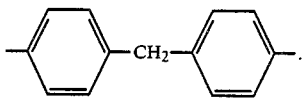

8. A compound of claim 5 wherein structure (a), A is

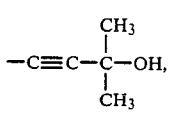

R is H and B is

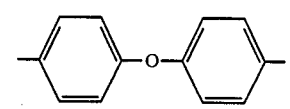

* * * * *

UNITED STATES PATENT AND TRADEMARK OFFICE
CERTIFICATE OF CORRECTION

PATENT NO. : 4,766,251

DATED : August 23, 1988

INVENTOR(S) : Robert D. Rossi and Steven P. Fenelli

It is certified that error appears in the above-identified patent and that said Letters Patent are hereby corrected as shown below:

In column 14, below line 66, add the following:

9. A compound of Claim 5 wherein structure (a), A is $$-C(CH_3)_2-C\equiv C-OH$$

, R is H and B is phenylene.

10. A compound of Claim 5 wherein structure (b), A is $$-C(CH_3)_2-C\equiv C-OH$$

, R is H and D is a cyclic or acyclic acetal radical.

UNITED STATES PATENT AND TRADEMARK OFFICE
CERTIFICATE OF CORRECTION

PATENT NO. : 4,766,251

DATED : August 23, 1988

INVENTOR(S) : Robert D. Rossi and Steven P. Fenelli

It is certified that error appears in the above-identified patent and that said Letters Patent is hereby corrected as shown below:

11. A compound of Claim 5 wherein structure (b), A is $-C\equiv CH$, R is H, and D is a cyclic acetal radical.

12. A compound of Claim 5 wherein structure (b), A is $-C\equiv CH$, R is H, and D is 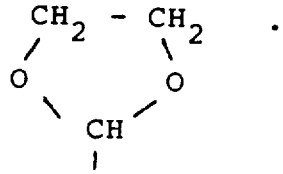

Signed and Sealed this

Seventh Day of February, 1989

*Attest:*

DONALD J. QUIGG

*Attesting Officer*     *Commissioner of Patents and Trademarks*